United States Patent [19]

Ahrens

[11] Patent Number: 4,705,520
[45] Date of Patent: Nov. 10, 1987

[54] IMPLANT

[75] Inventor: Uwe Ahrens, Berlin, Fed. Rep. of Germany

[73] Assignee: Mecron medizinische Produkte GmbH, Berlin, Fed. Rep. of Germany

[21] Appl. No.: 847,919

[22] Filed: Apr. 3, 1986

[30] Foreign Application Priority Data

Apr. 4, 1985 [DE] Fed. Rep. of Germany ... 8510531[U]

[51] Int. Cl.⁴ .............................................. A61F 2/36
[52] U.S. Cl. ........................................ 623/23; 623/18
[58] Field of Search .................. 623/22, 23, 16, 17, 623/18, 19, 20, 21; 128/92

[56] References Cited

U.S. PATENT DOCUMENTS

| | | | |
|---|---|---|---|
| 4,384,373 | 5/1983 | Swash | 623/18 |
| 4,459,708 | 7/1984 | Buttazzoni | 623/22 |
| 4,551,863 | 11/1985 | Murray | 623/23 |
| 4,586,932 | 5/1986 | Scales | 623/18 |

FOREIGN PATENT DOCUMENTS

| | | | |
|---|---|---|---|
| 0121491 | 10/1984 | European Pat. Off. | 623/22 |
| 854739 | 11/1952 | Fed. Rep. of Germany . | |
| 284588 | 9/1970 | Fed. Rep. of Germany . | |
| 3319916 | 5/1983 | Fed. Rep. of Germany . | |
| 1371335 | 10/1974 | United Kingdom . | |

Primary Examiner—Richard J. Apley
Assistant Examiner—David J. Isabella
Attorney, Agent, or Firm—Spencer & Frank

[57] ABSTRACT

Implant provided with a conical connection and means for releasing an element placed on the cone surface, particularly a joint ball, wherein the cone is provided with a longitudinal bore which opens into a transversely oriented opening, extends laterally to the outer surface, and is provided with a contact face facing the cone connection. A pin is provided which is displaceable in the longitudinal bore and, beginning at the front face of the cone, extends into the transversely oriented opening.

18 Claims, 5 Drawing Figures

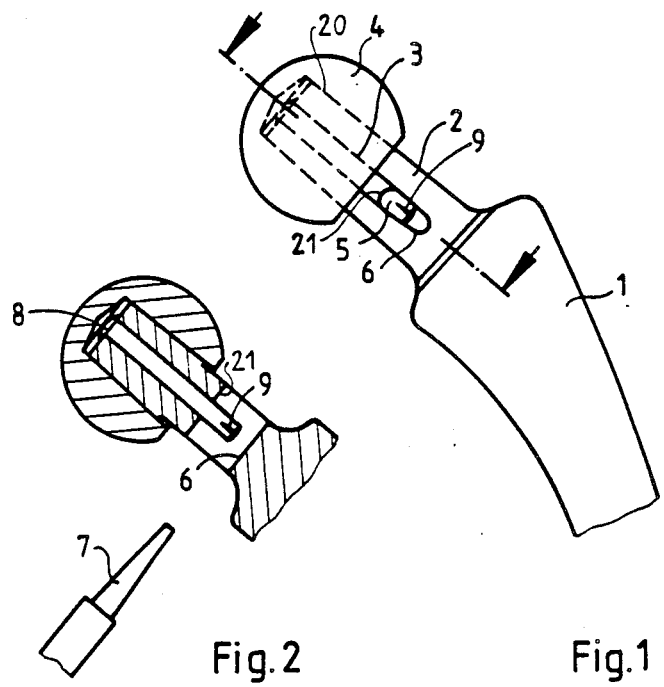
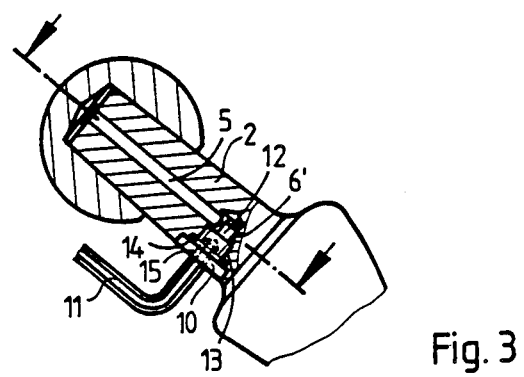
Fig. 2　Fig. 1
Fig. 3
Fig. 4　Fig. 5

IMPLANT

BACKGROUND OF THE INVENTION

The present invention relates to an implant of the type with an outer cone and having means for releasing an element placed on the outer cone, such as, for example, a joint ball.

In the treatment of human joints which are heavily impaired in function by trauma or illness, an endoprosthesis has found general acceptance. In recent years, endoprostheses have increasingly been provided with a cone onto which various heads can be plugged. These conical plug-in connections provide a very strong connection, even with very small attachment forces. However, in doing this, two primary problems appear:

1. After the ball of the joint is applied to the cone neck and the joint is repositioned, it is frequently noted during surgery that the length of the neck requires adjustment. To make this adjustment, the previously connected ball must be removed.

2. During subsequent surgery, it is often not necessary to replace the prosthesis stem. However, due to damage from frictional forces involved during use, it is advisable to also replace the used ball with an undamaged one.

The ball removing devices presently available on the market can each be used only for some of the implants and, in most cases, do not permit release of the plug-in ball without applying bending moments or forces to the shaft.

An implant of the above-mentioned type is disclosed in German Offenlegungsschrift (laid open patent application) No. 3,319,916, which shows an arrangement in which the joint ball is released by means of a nut which is screwed onto a threaded projection provided below the joint ball by "unscrewing" the nut by means of a tool in the direction toward the joint ball. This arrangement has the drawback that the nut provided directly below the joint ball in some cases limits the mobility of the joint or weakens the shaft perimeter in its outer regions which regions are of particular importance for its strength.

SUMMARY OF THE INVENTION

It is a object of the present invention to provide an implant with a means for releasing the joint ball from its cone seat which can be operated with simple tools and which does not influence the outer dimensions of the shaft and the ball.

A ball release mechanism has been developed which is integrated in the neck of the prosthesis and permits proper release of the joint ball for all types of balls presently in use without bending moments or forces acting on the prosthesis stem.

For this purpose, a central bore is made in the prosthesis neck, parallel to its longitudinal axis. Moreover, in its neck region not covered by the applied ball, the prosthesis is provided with a opening extending perpendicular to the longitudinal axis and meeting the central bore. An offset pin is inserted into the central bore and is prevented from falling out by a bead in its upper region.

Release of the attached joint ball is preferably effected by means of a wedge which is pressed into the long hole by means of a suitable instrument and drives the offset pin longitudinally along the bore and against the joint ball.

The particular advantage of the solution according to the invention is that the structurally simple solution does not influence the exterior mechanism and the effective contour of the connection between joint ball and shaft since the pin which may possibly release the joint ball is disposed centrally in the interior of the cone supporting the joint ball.

In preferred modifications of the invention, the pin is slightly broadened or curved toward the interior so that it will not drop out of the bore when the joint ball is removed, but can be driven in through the extension provided with the outer cone for the joint ball.

In another preferred embodiment of the invention, a screw is provided in a transverse bore instead of the wedge which must be driven transversely through the neck of the shaft. The shaft of this screw has a conically shaped or eccentric widened section which is not provided with a thread which contacts the upper portion of the offset pin. In this way, it is possible to produce rotation of the screw with a conventional tool (preferably a screwdriver for hollow screws) to drive the pin within the central bore provided in the neck of the prosthesis, thus pushing the joint ball off the neck.

It can be seen that the path to be traversed by the pin for releasing the joint ball is extremely short so that the lifting force to be transferred to the pin need not be very strong. Thus, even for a screw to be introduced into a transverse bore, a cone having only a relatively small slope ratio or a relatively slight eccentricity is required, provided that the cone has been manufactured with the necessary precision fit and thus the joint ball has a defined seat.

The means provided by the present invention can be used similarly for prosthesis construction sets which can be assembled in different lengths by means of cone plug-in connections, in which case the prosthesis shaft may also be composed of individual parts which are connected together by means of conical connections.

Advantageous features of the invention are defined in the claims and will be described in greater detail below together with a description of the preferred embodiment of the invention which is illustrated in the drawings.

BRIEF DESCRIPTION OF THE DRAWING

FIG. 1 is a side view of a first embodiment of the invention.

FIG. 2 is a sectional view of the embodiment of FIG. 1.

FIG. 3 is a detail sectional view of a further embodiment of the invention.

FIGS. 4 and 5 are detail sectional views of the further embodiment of the invention in a plane rotated by 90° with respect to the plane of FIG. 3.

DESCRIPTION OF THE PREFERRED EMBODIMENTS

FIG. 1 shows a hip joint prosthesis 1 which has a neck 2 provided with a longitudinal bore 3 which extends coaxially in the neck and is open, in the manner of a blind bore, toward the end of neck 2. The neck 2 is provided with a joint ball 4. Within bore 3 is provided a pin 5 which is displaceable in the longitudinal direction and can be accessed in the lower portion of neck 2, which portion is not covered by joint ball 4, through an opening 6 having an axis transverse to the bore axis.

The longitudinal bore 3, provided in the interior of the outer cone of the neck 2 and passing through the front face of cone 20 disposed at neck 2, has a configuration such that the opposite end of the bore opens into transverse opening 6. Opening 6 extends to the outer face of the neck 2 and has a contact face 21 facing the front face for engagement of a wedge or the like. This contact face 21 is generally formed by the face which delimits opening 6 and faces the cone connection.

Pin 5 which is displaceable in the longitudinal bore 3 extends, starting from the front face of the cone, into transverse opening 6. If a wedge is used, opening 6 is preferably a continuous opening.

The common region of bore 3 and opening 6 has a gradually decreasing cross-section in the direction away from the open end of the bore so that pin 5, provided in opening 3, cannot be moved completely down to the bottom of the transverse opening and the lower portion of transverse opening 6 thus remains open for the introduction of a wedge 7. The size relationships involved can be seen in the sectional view of FIG. 2.

Another possibility for preventing pin 5 from dropping down is to provide a slightly widened portion 8 (FIG. 2), in the manner of a rivet head, at its end facing the front face of the cone. In this way, the joint ball can always be removed quickly and without problems, should this be necessary during later surgery, by means of a wedge 7 that is tapped.

At its lower end, pin 5 has a slightly widened section 9 which is dimensioned in such a manner that pin 5 is prevented from dropping out of opening 3 when joint ball 4 is removed. This widened section 9 is produced through opening 6 by a punch mark in the center or by means of an appropriate sharp-edged instrument, after pin 5 has been inserted, thus seating it even more securely.

In the detail view of a further embodiment shown in FIG. 3, no tap is required to remove the joint ball; pin 5 can be actuated by means of a screw 10 which is driven with a screwdriver or wrench 11 for hollow screws (shown in dashed lines). Screw 10 is screwed into transverse opening 6' by means of a thread 13 and is provided with an eccentric 12 against which rests the end of pin 5. Depending on the position of eccentric 12, pin 5 is now pushed out along the bore in the direction of the joint ball, with the position of the eccentric being readable externally from a marking on the screw (not shown). The screw head is provided with a seal 14 which prevents the penetration of body fluids into the interior of neck 2 so that thickening or coagulation of such fluids does not impair functioning. Moreover, a polygonal recess is provided in the screw head to accommodate screwdriver or wrench 11.

FIGS. 4 and 5 shows eccentric 12 in the unraised and raised positions and it can be seen that, in FIG. 5, pin 5 has been raised for removal of joint ball 4.

The present invention is not limited to the above described preferred embodiments. Rather, a number of variations are conceivable which take advantage of the illustrated solution, even with basically different types of designs. This includes, in particular, different alternative devices for actuating pin 5. In addition to a wedge, a round instrument provided with a conical or eccentric shaft can be employed which is introduced in a correspondingly shaped recess. If the recess is provided with a thread 13, the advancing or holding forces exerted by the actuating instrument need not be generated externally. Rather, they are introduced directly into the prosthesis shaft. A simple example thereof is the herein illustrated screw 10 which either remains in the implant or forms a separate instrument which is used when required.

It will be understood that the above description of the present invention is susceptible to various modifications, changes and adaptations, and the same are intended to be comprehended within the meaning and range of equivalents of the appended claims.

I claim:

1. An implant comprising:
   (a) connection means having a cone shaped surface and
   (b) means for releasing from said connection means an element placed on the cone shaped surface, particularly a joint ball,
   (c) said means for releasing comprising a longitudinal bore in said connection means extending to a front face thereof, an opening at the surface of said connection means disposed in a direction transverse to said longitudinal bore, said bore communicating with said opening to provide an extension laterally to the outer surface of said cone, and
   (d) a pin displaceable in said longitudinal bore of length less than said bore and extending between the front face of the cone and the transversely oriented opening, whereby said pin is movable in said bore to extend out of said bore beyond said front face in response to a camming action thereon via said opening to release said element from connection on said cone shaped surface.

2. Implant as defined in claim 1, wherein the opening extending in the transverse direction extends through the connection means provided with the cone.

3. Implant as defined in claim 2, wherein the opening extending in the transverse direction has a larger dimension in the longitudinal direction than in the third spatial direction which is perpendicular to the longitudinal and to the transverse direction.

4. Implant as defined in claim 3, wherein the pin has one of a slightly curved configuration and at its end adjacent the transverse opening the cone is provided with a widened section projecting beyond the perimeter of the opening extending in the longitudinal direction.

5. Implant as defined in claim 4, wherein, at its end facing the cone connection, the pin has a widened section which projects beyond the perimeter of the opening extending in the longitudinal direction.

6. Implant as defined in claim 5, wherein the widened section is a frictionally secured section.

7. Implant as defined in claim 6, wherein the opening extending in the transverse direction has a thread into which a screw can be inserted.

8. Implant as defined in claim 7, wherein a screw inserted into the opening is provided with one of a conical and eccentric extension in the region of its shaft.

9. Implant as defined in claim 8, wherein the screw has a head, the head of the screw having an internal hexagon.

10. Implant comprising:
    connection means having a cone shaped surface;
    a bore disposed along a longitudinal axis of said connection means and extending to a front outer face thereof;
    an opening transverse to said axis extending to a surface of said connection means and communicating with said bore at portion thereof remote from said front outer face;

a prosthetic member frictionally secured to said connection means and extending thereover with said opening remaining externally exposed; and a pin disposed in said bore of length less than said bore, extending to said front outer face at one end thereof and extending to said opening at its other end, whereby said pin is movable in said bore to extend out of said bore beyond said front face in response to a camming action thereon via said opening to release said member from connection on said cone shaped surface.

11. Implant as defined in claim 10, wherein said pin includes means for restraining movement of one end thereof into said bore.

12. Implant as defined in claim 10, wherein said pin includes an enlarged portion at the end thereof within said bore to retain said pin at least partially within said bore.

13. Implant as defined in claim 11, wherein said pin includes an enlarged portion at the end thereof within said bore to retain said pin at least partially within said bore.

14. Implant as defined in claim 10 further including means disposable within said opening for moving said pin along said bore to remove said prosthetic member from said connection means.

15. Implant as defined in claim 11 further including means disposable within said opening for moving said pin along said bore to remove said prosthetic member from said connection means.

16. Implant as defined in claim 12 further including means disposable within said opening for moving said pin along said bore to remove said prosthetic member from said connection means.

17. Implant as defined in claim 13 further including means disposable within said opening for moving said pin along said bore to remove said prosthetic member from said connection means.

18. A two part endoprosthesis including a first ball joint having a conical blind bore formed therein terminating to an inner surface; a second elongated neck member, defining a longitudinal axis, for a plug in connection with said blind bore, including an outer conical surface terminating to a front face; said neck member having a longitudinal bore formed therein and extending between an opening in said front face and a transversely oriented opening in said outer surface spaced a predetermined distance from said front along the longitudinal axis face, and a pin means displaceable in said longitudinal bore and extending between said front face into said transversely oriented opening whereby insertion of a ball release means into said transversely oriented opening displaces said pin upon contact therewith a predetermined distance through said opening and contacting said inner surface thereby moving the ball joint in a direction away from said front face and releasing said ball joint from said neck portion.

* * * * *